United States Patent
Faryniarz et al.

(12) 
(10) Patent No.: US 6,495,123 B1
(45) Date of Patent: Dec. 17, 2002

(54) COSMETIC COMPOSITION WITH ORGANIC SUNSCREEN AND POROUS POWDER PARTICLES

(75) Inventors: Joseph Raymond Faryniarz, Middlebury, CT (US); Alan Joseph Suares, Cheshire, CT (US); Joanna Hong Zhang, Milford, CT (US); Michael Charles Cheney, Fairfield, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 10/144,997

(22) Filed: May 14, 2002

Related U.S. Application Data

(60) Provisional application No. 60/318,691, filed on Sep. 12, 2001.

(51) Int. Cl.$^7$ ............ A61K 7/42; A61K 7/44; A61K 7/00; A61K 31/74
(52) U.S. Cl. ............ 424/59; 60/400; 60/401; 60/78.02; 60/78.08
(58) Field of Search ............ 424/59, 60, 78.02, 424/78.08, 400, 401

(56) References Cited

U.S. PATENT DOCUMENTS 5,505,935 A    4/1996   Guerrero et al.

*Primary Examiner*—Shelley A. Dodson
(74) *Attorney, Agent, or Firm*—Milton L. Honig

(57) ABSTRACT

A cosmetic composition is provided which includes an organic sunscreen agent, a water-insoluble polymeric powder of porous particles, and an aqueous system wherein pH is less than 7. The porous particles remove the tackiness normally associated with organic sunscreen agents and low pH systems thereby providing a resultant composition of excellent skinfeel.

7 Claims, No Drawings

COSMETIC COMPOSITION WITH ORGANIC SUNSCREEN AND POROUS POWDER PARTICLES

This application claims the benefits of Provisional Application No. 60/318,691 filed Sep. 12, 2001.

BACKGROUND TO THE INVENTION

1. Field of the Invention

The invention concerns cosmetic compositions of improved aesthetic properties having low pH and containing organic sunscreen agents.

2. The Related Art

Sunscreen agents are commonly used in compositions intended for cosmetic application to the face and other exposed skin areas. These preparations are formulated as creams, lotions or oils containing as the agent an organic ultraviolet radiation absorbing chemical compound. The agent blocks passage of erythematogenic radiation thereby preventing its penetration into the skin.

High quality skinfeel properties are not always easy to achieve where the compositions contain sunscreen agents. The challenge is especially magnified with low pH systems. Organic sunscreens often have a sticky or tacky feel. These attributes must be counteracted when formulated into an aqueous emulsion composition. Formulating an aesthetically pleasant system incorporating these actives remains a challenge to chemists.

Sunscreen compositions have been well documented in the patent literature. For instance, U.S. Pat. No. 5,505,935 (Guerrero et at.) discloses sunscreen compositions wherein ethylene/vinyl acetate copolymer and poly(methyl methacrylate) particles were found useful as boosters for the sun protection factor (SPF).

Accordingly, it is an advantage of the present invention to provide an organic sunscreen agent formulated cosmetic composition with improved skinfeet, especially one with low tackiness.

Another advantage of the present invention is to provide a sunscreen agent formulated cosmetic composition that is an aqueous emulsion of low pH having good skinfeel properties.

These and other advantages of the present invention will become more apparent from consideration of the summary and detailed discussion which follows.

SUMMARY OF THE INVENTION

A cosmetic composition is provided which includes:

(i) from about 0.1 to about 15% by weight of an organic sunscreen agent having a chromophoric group active within the ultraviolet radiation range from 290 to 400 nm;

(ii) from about 0.01 to about 10% by weight of a water-insoluble powdered polymer formed as porous particles having an Oil Absorbance (castor oil) value ranging from about 90 to about 500 ml/100 gm; and (iii) from about 1 to about 99% of water, the composition having a pH of less than 7.

DETAILED DESCRIPTION OF THE INVENTION

Now it has been found that water-insoluble polymeric powders in porous particle form can modify the tacky skinfeel normally associated with organic sunscreen agents. Excellent skinfeel without any perceptible tackiness is achieved, even in systems having extremely low pH.

A first element of compositions according to the present invention is that of a water-insoluble material in the form of polymeric porous spherical particles. By the term "porous" is meant an open or closed cell structure. Preferably the particles are not hollow beads. Average particle size may range from about 0.1 to about 100, preferably from about 1 to about 50, more preferably greater than 5 and especially from 5 to about 15, optimally from about 6 to about 10 micron. Organic polymers or copolymers are the preferred materials and can be formed from monomers including the acid, salt or ester forms of acrylic acid, methacrylic acid, methylacrylate, ethylacrylate, ethylene, propylene, vinylidene chloride, acrylonitrile, maleic acid, vinyl pyrrolidone, styrene, butadiene and mixtures thereof. The polymers are especially useful in cross-linked form. Cells of the porous articles may be filled by a gas which can be air, nitrogen or a hydrocarbon. Oil Absorbance (castor oil) is a measure of porosity and may range from about 90 to about 500, preferably from about 100 to about 200, optimally from about 120 to about 180 ml/100 grams. Density of the particles may range from about 0.08 to 0.55, preferably from about 0.15 to 0.48 g/cm$^3$.

Illustrative porous polymers include polymethylmethacrylate and cross-linked polystyrene. Most preferred is polymethyl methacrylate available as Ganzpearl® 820 available from Presperse, Inc., Piscataway, N.J., known also by its INCI name of Methyl Methacrylate Crosspolymer.

Amounts of the water-insoluble polymeric porous particles may range from about 0.01 to about 10%, preferably from about 0.1 to about 5%, optimally from about 0.3 to about 2% by weight of the composition.

A second element of compositions according to the present invention is that of an organic sunscreen agent having at least one chromophoric group absorbing within the ultraviolet ranging from 290 to 400 nm. Chromophoric organic sunscreen agents may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyt, terpinyl, and cyclohexenyl esters); Salicylates (octyl, amyl, phenyl, benzyl, menthyl, glyceryl, and dipropyleneglycol esters);

Cinnamic acid derivatives (menthyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2', 4,4'-

Tetrahydroxybenzophenone, 2,2'-Dihydroxy-4,4'-dimethoxybenzophenone, Octabenzone; 4-lsopropyldibenzoylmethane; Butylmethoxydibenzoylmethane; Etocrylene; and 4-isopropyl-dibenzoylmethane).

Particularly useful are: 2-ethylhexyl p-methoxycinnamate, 4,4'-t-butyl methoxydibenzoylmethane, 2-hydroxy-4-methoxybenzophenone, octyidimethyl p-aminobenzoic acid, digalloyLtrioleate, 2,2-dihydroxy-4-methoxybenzophenone, ethyl 4-[bis(hydroxypropyt)] aminobenzoate, 2-ethylhexyl-2-cyano-3,3-diphenylacrylate, 2-ethythexylsalicytate, glyceryl p-aminobenzoate, 3,3,5-trimethytcyclohexylsaticylate, methylanthranitate, p-dimethylaminobenzoic acid or aminobenzoate, 2-ethylhexyl p-dimethylaminobenzoic, 2-phenytbenzimidazole-5-sulfonic acid, 2-(p-dimethylaminophenyl)-5-sulfoniobenzoxazoic acid and mixtures thereof.

Suitable commercially available organic sunscreen agents are those identified under the following table.

TABLE I

| CTFA NAME | TRADE NAME | SUPPLIER |
|---|---|---|
| Benzophenone-3 | UVINUL M-40 | BASF Chemical Co. |
| Benzophenone-4 | UVINUL MS-40 | BASF Chemical Co. |
| Benzophenone-8 | SPECTRA-SORB UV-24 | American Cyanamid |
| DEA-Methoxycinnamate | BERNEL HYDRO | Bernel Chemical |
| Ethyl dihydroxypropyl-PABA | AMERSCREEN P | Amerchol Corp. |
| Glyceryl PABA | NIPA G.M.P.A. | Nipa Labs. |
| Homosatate | KEMESTER HMS | Humko Chemical |
| Menthyl anthranilate | SUNAROME UVA | Fetton Worldwide |
| Octocrylene | UVINUL N-539 | BASF Chemical Co. |
| Octyl dimethyl PABA | AMERSCOL | Amerchol Corp. |
| Octyl methoxycinnamate | PARSOL MCX | Bernel Chemical |
| Octyl salicylate | SUNAROME WMO | Fetton Worldwide |
| PABA | PABA | National Starch |
| 2-Phenylbenzimidazole-5-sulphonic acid | EUSOLEX 232 | EM Industries |
| TEA salicylate | SUNAROME W | Fetton Worldwide |
| 2-(4-Methylbenzylidene)-camphor | EUSOLEX 6300 | EM Industries |
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Butyl methoxy dibenzoyl methane | PARSOL 1789 | Givaudan Corp. |
| Etocrylene | UVINUL N-35 | BASF Chemical Co. |

Amounts of the organic sunscreen agent will range from about 0.1 to about 15%, preferably from about 0.5% to about 10%, optimally from about 1% to about 8% by weight of the composition.

Compositions of the present invention wilt contain water in amounts 5 from about 1 to about 99%, preferably from about 5 to about 90%, more preferably from about 35 to about 70%, optimally between about 40 and about 60% by weight. Ordinarily the compositions will be water and oil emulsions of the W/O or O/W variety.

Compositions of the present invention wilt have a pH less than 7, preferably ranging from about 1 to 6.8, more preferably ranging from about 1 to about 6.5, still more preferably from about 2.5 to about 4.5, optimally from about 3 to about 3.8.

Where the compositions are emulsions, they may comprise emollient materials in the form of mineral oils, silicone oils and synthetic or natural esters. Amounts of the emollients may range from about 0.1 to about 30%, preferably between about 0.5 and 20% by weight.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C.

Among suitable ester emollients are:
(1) Alkenyl or alkyl esters of fatty acids having 10 to 20 carbon atoms. Examples thereof include isopropyl palmitate, isopropyl isostearate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate.
(5) Sterols esters, of which soya sterol and cholesterol fatty acid esters are examples thereof.

The most preferred esters are dicaprytyl ether and isopropyl isostearate.

Fatty acids having from 10 to 30 carbon atoms may also be included in the compositions of this invention. Illustrative of this category are pelargonic, tauric, myristic, palmitic, stearic, isostearic, hydroxystearic, oleic, linoleic, ricinoleic, arachidic, behenic and erucic acids.

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include glycerol (also known as glycerin), polyalkylene glycols and more preferably alkylene polyols and their derivatives, including propytene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably glycerin. The amount of humectant may range anywhere from 0.5 to 30%, preferably between 1 and 15% by weight of the composition.

Cosmetic compositions of the present invention may be in any form. These forms may include lotions, creams, roll-on formulations, mousses, aerosol sprays and cloth- or pad-apptied formulations.

Emulsifiers may also be present in cosmetic compositions of the present invention. Total concentration of the emulsifier may range from about 0.1 to about 40%, preferably from about 1 to about 20%, optimally from about 1 to about 5% by weight of the total composition. The emulsifier may be selected from the group consisting of anionic, nonionic, cationic and amphoteric actives. Particularly preferred non-ionic surfactants are those with a $C_{10}$–$C_{20}$ fatty alcohol or acid hydrophobe condensed with from about 2 to about 100 moles of ethylene oxide or propylene oxide per mote of hydrophobe; $C_2$–$C_{10}$ alkyl phenols condensed with from 2 to 20 motes of alkylene oxide; mono- and di- fatty acid esters of ethylene glycol; fatty acid monoglyceride; sorbitan, mono- and di- $C_8$–$C_{20}$ fatty acids; and polyoxyethylene sorbitan as well as combinations thereof. Alkyl polyglycosides and saccharide fatty amides (e.g. methyl gluconamides) are also suitable nonionic emulsifiers.

Preferred anionic emulsifiers include soap, alkyl ether sulfate and sulfonates, alkyl sulfates and sulfonates, alkylbenzene sulfonates, alkyl and dialkyt sulfosuccinates, $C_8$–$C_{20}$ acyl isethionates, $C_8$–$C_{20}$ alkyl ether phosphates, alkylethercarboxylates and combinations thereof.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition.

Thickening agents may be included in compositions of the present invention. Particularly useful are the polysaccharides. Examples include starches, natural/synthetic gums and cellulosics. Representative of the starches are chemically modified starches such as aluminum starch octenylsuccinate. Suitable gums include xanthan, sclerotium, pectin, karaya, arabic, agar, guar, carrageenan, alginate and combinations thereof. Suitable cellulosics include hydroxypropyl cellulose, hydroxypropyl methylcellulose, ethylcellulose and sodium carboxy methylcellulose. Synthetic polymers are still a further class of effective thickening agent. This category includes crosslinked polyacrylates such as the Carbomers, polyacrylamides such as Sepigel® 305 and taurate copolymers such as Aristoflex® AVC, the latter identified by its INCI nomenclature of Acryloyl Dimethyltaurate/Vinyl Pyrrolidone Copolymer.

Amounts of the thickener may range from about 0.001 to about 5%, preferably from about 0.1 to about 2%, optimally from about 0.2 to about 0.5% by weight.

For additional thickening, it is preferred to have magnesium aluminum silicate, commercially available as Veegum®, sold by the R.T. Vanderbilt Company. Amounts of this inorganic thickening agent may range from about 0.01 to about 10%, preferably from about 0.5 to about 1.2% by weight.

Optionally the compositions may include an alpha- or beta-hydroxycarboxylic acid. Most preferred are the free acid, salts or esters of glycolic acid, lactic acid, 2-hydroxyoctanoic acid, gluconolactone and mixtures thereof. Amounts of these materials may range from about 0.01 to about 20%, preferably from about 0.2 to about 10%, optimally from about 1 to about 5% by weight.

Minor adjunct ingredients may also be present in the cosmetic compositions. Among them may be the vitamins such as Vitamin A Palmitate, Vitamin C and derivatives (e.g. ascorbyl palmitate or magnesium ascorbyl phosphate), Vitamin E Acetate and DL-panthenol. Also useful are: retinol, ceramides and herbal extracts including green tea and chamomile.

Colorants, fragrances and abrasives may also be included in compositions of the present invention. Each of these substances may range from about 0.05 to about 5%, preferably between 0.1 and 3% by weight.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

The following Examples will more fully illustrate the embodiments of this invention. All parts, percentages and proportions referred to herein and in the appended claims are by weight unless otherwise indicated.

EXAMPLES 1–8

Typical formulations according to the present invention are described below.

| | Example (Weight %) | | | | | | | |
|---|---|---|---|---|---|---|---|---|
| Ingredients | 1 | 2 | 3 | 4 | 5 | 6 | 7 | 8 |
| Disodium EDTA | 0.05 | 0.05 | 0.05 | 0.05 | 0.05 | 0.05 | 0.05 | 0.05 |
| Methyl Paraben | 0.15 | 0.15 | 0.15 | 0.15 | 0.15 | 0.15 | 0.15 | 0.15 |
| Aloe Vera | 0.10 | 0.10 | 0.10 | 0.10 | 0.10 | 0.10 | 0.10 | 0.10 |
| Magnesium Aluminum Silicate | 0.60 | 0.60 | 0.60 | 0.60 | 0.60 | 0.60 | 0.60 | 0.60 |
| Glycerin | 5.00 | 5.00 | 5.00 | 5.00 | 5.00 | 5.00 | 5.00 | 5.00 |
| Butylene Glycol | 2.00 | 2.00 | 2.00 | 2.00 | 2.00 | 2.00 | 2.00 | 2.00 |

-continued

| Ingredients | Example (Weight %) | | | | | | | |
|---|---|---|---|---|---|---|---|---|
| | 1 | 2 | 3 | 4 | 5 | 6 | 7 | 8 |
| Xanthan Gum | 0.20 | 0.20 | 0.20 | 0.20 | 0.20 | 0.20 | 0.20 | 0.20 |
| Cetearyl Alcohol | 1.50 | 1.50 | 1.50 | 1.50 | 1.50 | 1.50 | 1.50 | 1.50 |
| Sorbitan Stearate | 1.10 | 1.10 | 1.10 | 1.10 | 1.10 | 1.10 | 1.10 | 1.10 |
| PEG-100 Stearate | 0.50 | 0.50 | 0.50 | 0.50 | 0.50 | 0.50 | 0.50 | 0.50 |
| Glyceryl Dilaurate | 0.50 | 0.50 | 0.50 | 0.50 | 0.50 | 0.50 | 0.50 | 0.50 |
| Stearic Acid | 3.00 | 3.00 | 3.00 | 3.00 | 3.00 | 3.00 | 3.00 | 3.00 |
| Sucrose Polystearate | 0.25 | 0.25 | 0.25 | 0.25 | 0.25 | 0.25 | 0.25 | 0.25 |
| Propylparaben | 0.10 | 0.10 | 0.10 | 0.10 | 0.10 | 0.10 | 0.10 | 0.10 |
| Tocopheryl Acetate | 0.10 | 0.10 | 0.10 | 0.10 | 0.10 | 0.10 | 0.10 | 0.10 |
| Ascorbyl Palmitate | 0.01 | 0.01 | 0.01 | 0.01 | 0.01 | 0.01 | 0.01 | 0.01 |
| Octyl Methoxycinnamate | 2.00 | 1.00 | 2.00 | 4.00 | 4.00 | 1.00 | 2.00 | 2.00 |
| Dimethicone | 1.00 | 2.00 | 1.00 | 0.50 | 3.00 | 1.00 | 5.00 | 1.00 |
| Dicaprylyl Ether | 4.00 | 3.00 | 6.00 | 6.00 | 2.00 | 3.00 | 0.50 | 0.50 |
| Isopropyl Isostearate | 1.50 | 1.50 | 1.50 | 1.50 | 1.50 | 1.50 | 1.50 | 1.50 |
| Glycolic Acid (80% Active) | 8.00 | 11.40 | 8.40 | 4.60 | 10.60 | 12.40 | 10.80 | 8.80 |
| Ammonium Hydroxide | 1.80 | 2.80 | 1.80 | 0.50 | 2.40 | 3.00 | 2.50 | 1.80 |
| Polymethyl Methacrylate (Ganzpearl ® 820) | 1.00 | 0.50 | 0.50 | 1.50 | 1.50 | 3.00 | 3.00 | 0.10 |
| Aluminum Starch Octenylsuccinate | 2.00 | 2.00 | 3.00 | 1.50 | 0.50 | 3.00 | 2.50 | 2.00 |
| Acryloyl Dimethyltaurate Copolymer (7% Active) | 1.00 | 1.30 | 1.50 | 2.00 | 4.00 | 0.50 | 0.50 | 1.00 |
| Bisabolol | 0.10 | 0.10 | 0.10 | 0.10 | 0.10 | 0.10 | 0.10 | 0.10 |
| Retinol | 0.02 | 0.02 | 0.02 | 0.02 | 0.02 | 0.02 | 0.02 | 0.02 |
| Fragrance | 0.03 | 0.03 | 0.03 | 0.03 | 0.03 | 0.03 | 0.03 | 0.03 |
| Water | Balance | Balance | Balance | Balance | Balance | Balance | Balance | Balance |

EXAMPLE 9

Comparative experiments are presented herein against the COVABEADS product of LCW, a Sensient Company. COVABEAD is a polymethylmethyacrylate solid non-porous spherical particle. Oil Absorbance (castor oil) of the COVABEAD particles is 80 ml/100 grams. This particle was compared to that of the present invention, namely Ganzpearl® 820 (identified in the Tables below as GMP 0820) which is a porous particle with Oil Absorbance (castor oil) of 170 ml/100 gm. These particles were evaluated in a base formula whose components are listed in Table I.

TABLE I

| Ingredient Name | Weight % |
|---|---|
| Phase A | |
| Mineral Water Extract | 0.10 |
| Disodium EDTA | 0.10 |
| Dl Panthenol | 0.20 |
| Sodium Lactate | 0.10 |
| Sodium PCA (50% in water) | 0.20 |
| Green Tea Extract | 0.10 |
| Grapeseed Extract | 0.10 |
| Glycerin | 5.00 |
| Water | Balance |
| Phase B | |
| Carbopol Ultrez 10 ® | 0.50 |
| Phase C | |
| Triethanolamine (99% active) | 2.10 |
| Parsol HS ® | 2.00 |
| Deionized Water | 10.00 |
| Phase D | |
| Myristyl Alcohol | 0.50 |
| Sorbitan Stearate | 1.10 |
| Cetyl Alcohol | 0.50 |
| Glyceryl Dilaurate | 0.50 |
| Stearyl Alcohol | 0.50 |
| Sucrose Stearate | 0.50 |
| PEG-100 Stearate | 0.50 |
| Stearic Acid | 0.25 |
| Vitamin E Acetate | 0.20 |
| Linolieic Acid | 0.10 |
| Linoleamide MEA | 0.10 |
| Cholesterol | 0.20 |
| Phase E | |
| Parsol MCX ® | 5.5 |
| Dermablock OS ® | 3 |
| Parsol 1789 ® | 2 |
| Phase F | |
| Permethyl 99A ® | 4.50 |
| Phase G | |
| Water | 0.50 |
| Ceramide/Phylosphingosine Mixture | 0.01 |
| Phase H | |
| Iodopropynyl Butyl Carbamate | 0.10 |
| Phenoxyethanol | 0.60 |
| Phase I | |
| Bisalolol | 0.20 |
| Vitamin A Palmitate | 0.01 |
| Fragrance | 0.30 |

The base formula was prepared by charging a main beaker with Phase A. This was mixed and stirred until homogeneous at 75–80° C. Phase B was added to the stirred Phase A and mixed until dispersed. Temperature was maintained while charging Phase C into the main beaker. Agitation was continued until all components were uniformly dispersed. Phase D was then melted and mixed at 75° C. Phase E was pre-mixed and the polymethylmethacrylate particles of either COVABEAD or Ganzpearl® were heated at 75° C. and then added to Phase D. The resultant combined Phases D/E were then added to the main beaker under homogenization conditions for five minutes. Phase F was then added to the main batch and homogenization continued for an additional five minutes. The batch was cooled to 40–45° C. whereupon Phases G and H were added. Temperature was reduced to 35° C. and Phase I combined into the mixture until completely uniform.

A clinical study was conducted with an expert panel of n panelists evaluating skinfeel properties of the base formula with different levels of COVABEADS and Ganzpearl® 820. Results are reported in the Tables below.

TABLE II

Product That Rubs in Faster*

| Product (n = 9) | Frequency |
| --- | --- |
| 1.5% GMP 0820 | 4 |
| 1.5% COVABEAD | 4 |
| No Difference | 1 |

| Product (n = 8) | Frequency |
| --- | --- |
| 0.5% GMP 0820 | 4 |
| 0.5% COVABEAD | 2 |
| No Difference | 2 |

| Product (n = 10) | Frequency |
| --- | --- |
| 1.0% GMP 0820 | 2 |
| 1.0% COVABEAD | 6 |
| No Difference | 2 |

| Product (n = 9) | Frequency |
| --- | --- |
| 2.0% GMP 0820 | 5 |
| 2.0% COVABEAD | 4 |
| No Difference | 0 |

*For the product chosen above, how much faster
1 = "Slightly Faster",
5 = "Much Faster"

TABLE III

Feels Drier to the Touch During Application*

| Product | Frequency |
| --- | --- |
| 1.5% GMP 0820 | 7 |
| 1.5% COVABEAD | 0 |
| No Difference | 2 |
| 0.5% GMP 0820 | 4 |
| 0.5% COVABEAD | 1 |
| No Difference | 3 |
| 1.0% GMP 0820 | 4 |
| 1.0% COVABEAD | 4 |
| No Difference | 2 |
| 2.0% GMP 0820 | 6 |
| 2.0% COVABEAD | 3 |
| No Difference | 0 |

*For the Product Chosen Above, How Much Drier
1 = "Slightly Drier",
5 = "Much Drier"

TABLE IV

Feels Less Oily During Application*

| Product | Frequency |
| --- | --- |
| 1.5% GMP 0820 | 6 |
| 1.5% COVABEAD | 1 |
| No Difference | 2 |
| 0.5% GMP 0820 | 3 |
| 0.5% COVABEAD | 2 |
| No Difference | 3 |

TABLE IV-continued

Feels Less Oily During Application*

| Product | Frequency |
| --- | --- |
| 1.0% GMP 0820 | 5 |
| 1.0% COVABEAD | 2 |
| No Difference | 3 |
| 2.0% GMP 0820 | 6 |
| 2.0% COVABEAD | 1 |
| No Difference | 2 |

*For the Product Chosen Above, How Much Less Oily
1 = "Slightly Less Oily",
5 = Much Less Oily"

TABLE V

Feels Less Sticky During Rub In*

| Product | Frequency |
| --- | --- |
| 1.5% GMP 0820 | 3 |
| 1.5% COVABEAD | 1 |
| No Difference | 5 |
| 0.5% GMP 0820 | 2 |
| 0.5% COVABEAD | 3 |
| No Difference | 3 |
| 1.0% GMP 0820 | 8 |
| 1.0% COVABEAD | 1 |
| No Difference | 1 |
| 2.0% GMP 0820 | 8 |
| 2.0% COVABEAD | 0 |
| No Difference | 1 |

*For the Product Chosen Above, How Much Less Sticky
1 = "Slightly Less Sticky",
5 = "Much Less Sticky"

TABLE VI

Feels Less Sticky on Face*

| Product | Frequency |
| --- | --- |
| 1.5% GMP 0820 | 3 |
| 1.5% COVABEAD | 2 |
| No Difference | 4 |
| 0.5% GMP 0820 | 3 |
| 0.5% COVABEAD | 3 |
| No Difference | 2 |
| 1.0% GMP 0820 | 4 |
| 1.0% COVABEAD | 3 |
| No Difference | 3 |
| 2.0% GMP 0820 | 5 |
| 2.0% COVABEAD | 2 |
| No Difference | 2 |

*For the Product Chosen Above, How Much Less Sticky
1 = "Slightly Less Sticky",
5 = "Much Less Sticky"

TABLE VII

Feels Less Oily On Face*

| Product | Frequency |
| --- | --- |
| 1.5% GMP 0820 | 7 |
| 1.5% COVABEAD | 1 |
| No Difference | 1 |
| 0.5% GMP 0820 | 2 |
| 0.5% COVABEAD | 2 |
| No Diffence | 4 |
| 1.0% GMP 0820 | 4 |
| 1.0% COVABEAD | 4 |

TABLE VII-continued

Feels Less Oily On Face*

| Product | Frequency |
|---|---|
| No Difference | 2 |
| 2.0% GMP 0820 | 6 |
| 2.0% COVABEAD | 2 |
| No Difference | 1 |

*For the Product Chosen Above, How Much Less Oily
1 = "Slightly Less Oily",
5 = "Much Less Oily"

TABLE VIII

Feels Drier on Face*

| Product | Frequency |
|---|---|
| 1.5% GMP 0820 | 6 |
| 1.5% COVABEAD | 1 |
| No Difference | 1 |
| 0.5% GMP 0820 | 4 |
| 0.5% COVABEAD | 2 |
| No Difference | 2 |
| 1.0% GMP 0820 | 5 |
| 1.0% COVABEAD | 3 |
| No Difference | 2 |
| 2.0% GMP 0820 | 5 |
| 2.0% COVABEAD | 3 |
| No Difference | 1 |

*For the Product Chosen Above, How Much Drier
1 = "Slightly Drier",
5 = "Much Drier"

TABLE IX

Overall Preference

| Product | Frequency |
|---|---|
| 1.5% GMP 0820 | 4 |
| 1.5% COVABEAD | 2 |
| No Preference | 3 |
| 0.5% GMP 0820 | 5 |
| 0.5% COVABEAD | 1 |
| No Preference | 2 |
| 1.0% GMP 0820 | 5 |
| 1.0% COVABEAD | 2 |
| No Preference | 3 |
| 2.0% GMP 0820 | 5 |
| 2.0% COVABEAD | 1 |
| No Preference | 3 |

In general, the expert panel for most of the concentration range tested found the GanzpearL® 820 (GMP 0820) formulation preferable over the one with COVABEADS. Particularly, the panelists considered Ganzpearl® 820 superior in the attributes of "feels dryer to the touch during application", "feels less oily during application", "feels less oily on face", "feels dryer on face" and in "overall preference".

The foregoing description and examples illustrate selected embodiments of the present invention. In light thereof variations and modifications will be suggested to one skilled in the art, all of which are within the spirit and purview of this invention.

What is claimed is:

1. A cosmetic composition comprising:
   (i) from about 0.1 to about 15% by weight of an organic sunscreen agent having a chromophoric group active within the ultraviolet radiation range from 290 to 400 nm;
   (ii) from about 0.01 to about 10% by weight of a water-insoluble powdered polymer formed as porous particles having an Oil Absorbance (castor oil) value ranging from about 90 to about 500 ml/100 gm; and
   (iii) from about 1 to about 99% of water, the composition having a pH of less than 7.

2. A composition according to claim 1 wherein the sunscreen agent is octyl methoxycinnamate.

3. A composition according to claim 1 wherein the water-insoluble particles are organic polymers formed from a monomer selected from the group consisting of acrylic acid, methacrylic acid, methylacrylate, ethylacrylate, ethylene, propylene, vinylidene chloride, acrylonitrile, maleic acid, vinyl pyrrolidone, styrene, butadiene and mixtures thereof.

4. A composition according to claim 1 wherein the polymeric particles are polymethyl methacrylate.

5. A composition according to claim 1 wherein the particles are cross-linked.

6. A composition according to claim 1 wherein the particles have an Oil Absorbance value ranging from about 100 to about 200 ml/100 gm.

7. A cosmetic composition comprising:
   (i) from about 0.1 to about 15% by weight of an organic sunscreen agent having a chromophoric group active within the ultraviolet radiation range from 290 to 400 nm;
   (ii) from about 0.01 to about 10% by weight of a water-insoluble powdered polymethyl methacrylate polymer formed as porous particles having an Oil Absorbance (castor oil) value ranging from about 100 to about 200 ml/100 gm; and
   (iii) from about 1 to about 99% of water, the composition having a pH ranging from about 1 to about 6.5.

* * * * *